US010583246B2

(12) United States Patent
Zager et al.

(10) Patent No.: US 10,583,246 B2
(45) Date of Patent: Mar. 10, 2020

(54) HIGH FLOW RATE ISOLATED INFUSION FOR REGIONAL TREATMENT OF CANCER AND MEDICAL CONDITIONS

(75) Inventors: Jonathan Zager, Tampa, FL (US); Stephen Stewart, Harmony, PA (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 758 days.

(21) Appl. No.: 14/003,932

(22) PCT Filed: Mar. 9, 2012

(86) PCT No.: PCT/US2012/028481
§ 371 (c)(1),
(2), (4) Date: Sep. 9, 2013

(87) PCT Pub. No.: WO2012/122475
PCT Pub. Date: Sep. 13, 2012

(65) Prior Publication Data
US 2013/0345675 A1    Dec. 26, 2013

Related U.S. Application Data

(60) Provisional application No. 61/450,895, filed on Mar. 9, 2011.

(51) Int. Cl.
*A61M 5/142*    (2006.01)
*A61M 5/44*    (2006.01)
(Continued)

(52) U.S. Cl.
CPC ........ *A61M 5/14276* (2013.01); *A61M 5/142* (2013.01); *A61M 5/168* (2013.01);
(Continued)

(58) Field of Classification Search
CPC .... A61M 5/44; A61M 5/14276; A61M 5/168; A61M 5/142; A61M 5/16831; A61M 5/145
See application file for complete search history.

(56) References Cited

U.S. PATENT DOCUMENTS 4,747,826 A * 5/1988 Sassano .................. A61M 5/44
128/DIG. 12
5,411,479 A * 5/1995 Bodden ............... A61M 1/3621
604/101.03
(Continued)

OTHER PUBLICATIONS

"Optimizing regional infusion treatment strategies for melanoma of the extremities", Andrew Coleman, BSc, MA, MHS, Christina K Augustine, PhD, Georgia Beasley, MD, Gretchen Sanders, RN, andDouglas Tyler, MD, Expert Rev Anticancer Ther. Nov. 2009; 9(11): 1599. (Year: 2009).*

(Continued)

*Primary Examiner* — Brandy S Lee
(74) *Attorney, Agent, or Firm* — Meunier Carlin & Curfman LLC

(57) ABSTRACT

The present application relates to high flow rate isolated regional treatment of cancer and proliferative disorders and conditions. For example, provided are methods, systems and devices for treating a cancer in a region of a subject using high flow rate isolated infusion.

16 Claims, 3 Drawing Sheets

(51) Int. Cl.
 *A61M 5/168* (2006.01)
 *A61M 5/145* (2006.01)
(52) U.S. Cl.
 CPC .............. *A61M 5/44* (2013.01); *A61M 5/145* (2013.01); *A61M 5/16831* (2013.01)

(56) References Cited

U.S. PATENT DOCUMENTS

| | | | | |
|---|---|---|---|---|
| 5,569,182 | A * | 10/1996 | Twardowski | A61M 5/1582 604/264 |
| 5,817,046 | A | 10/1998 | Glickman | |
| 5,833,658 | A * | 11/1998 | Levy | A61M 25/1011 604/97.01 |
| 6,406,267 | B1 * | 6/2002 | Mondiere | F04B 43/0072 417/53 |
| 2002/0107504 | A1 * | 8/2002 | Gordon | A61M 31/005 604/507 |
| 2003/0049135 | A1 * | 3/2003 | Gray | A61M 5/14216 417/44.1 |
| 2004/0082908 | A1 * | 4/2004 | Whitehurst | A61M 5/14276 604/67 |
| 2005/0234431 | A1 * | 10/2005 | Williams | A61M 5/14276 604/890.1 |
| 2009/0054823 | A1 * | 2/2009 | Bridges | A61M 1/3621 604/6.09 |
| 2011/0257577 | A1 * | 10/2011 | Lane | A61M 1/3653 604/6.11 |

OTHER PUBLICATIONS

Brady, et al., "Isolated limb infusion with melphalan and dactinomycin for regional melanoma and soft-tissue sarcoma of the extremity: final report of a phase II clinical trial," Melanoma Res., Apr. 2009, 19(2):106-111.

Chai, et al., "A multi-institutional experience of repeat regional chemotherapy for recurrent melanoma of extremities," Ann Surg Oncol, May 2013, 19(5):1637-43.

Deneve, et al., "Isolated regional therapy for advanced extremity soft tissue sarcomas," Surg Oncol Clin N Am, Apr. 2012, 21(2):287-99.

Han, et al., "Minimally invasive intra-arterial regional therapy for metastatic melanoma: isolated limb infusion and percutaneous hepatic perfusion," Expert Opin Drug Metab Toxicol, Nov. 2011, 7(11):1383-94.

Moller, et al., "Toxicities associated with hyperthermic isolated limb perfusion and isolated limb infusion in the treatment of melanoma and sarcoma," Intl J Hyperthermia, May 2008, 24(3):275-89.

Santillan, et al., "Predictive Factors of Regional Toxicity and Serum Creatine Phosphokinase Levels After Isolated Limb Infusion for Melanoma: A Multi-Institutional Analysis," Annals Surg Oncol, Sep. 2009, 16(9):2570-78.

Turaga, et al., "Limb preservation with isolated limb infusion for locally advanced nonmelanoma cutaneous and soft-tissue malignant neoplasms," Arch Surg, Jul. 2011, 146(7):870-75.

Vohra, et al., "The use of isolated limb infusion in limb threatening extremity sarcomas," Int J Hyperthermia, 2013, 29(1):1-7.

Vyas, et al., "Isolated limb infusion with cytotoxic agents: A Simplified Approach for Venous Access," Cancer, Nov. 18, 2010, 116(2):459-464.

Wong, et al., "Isolated limb infusion in a series of over 100 infusions: a single-center experience," Ann Surg Oncol, Apr. 2013, 20(4):1121-27.

Wong, et al., "Resection of Residual Disease after Isolated Limb Infusion (ILI) Is Equivalent to a Complete Response after ILI-Alone in Advanced Extremity Melanoma," Ann Surg Oncol, Feb. 2014, 21(2):650-55.

* cited by examiner

HIGH FLOW RATE ISOLATED INFUSION FOR REGIONAL TREATMENT OF CANCER AND MEDICAL CONDITIONS

CROSS REFERENCE TO RELATED APPLICATIONS

This application claims the benefit of U.S. Provisional Application No. 61/450,895, filed on Mar. 9, 2011, and is a 371 National phase of PCT US2012/028481, filed Mar. 9, 2012, both of which are incorporated by reference herein in their entirety.

TECHNICAL FIELD

The present application relates to regional treatment of cancer and proliferative disorders and conditions.

BACKGROUND

Isolated limb perfusion (ILP) and isolated limb infusion (ILI) are alternative approaches for regional chemotherapy treatment.

During ILP the limb vasculature is isolated from that of the rest of the body and a high dose of a chemotherapeutic agent (e.g. melphalan) can be delivered to the tumor-bearing tissues. Regional drug concentrations can be administered up to a 10-fold of what is tolerated systemically. Due to the isolation of the limb, systemic toxicity is absent or negligible. Isolation is achieved by ligation or temporary occlusion of collateral blood vessels and the placement of a proximal tourniquet. The limb blood flow is then pumped through an oxygenator and a heat exchanger in an external circuit to provide oxygenated and temperature regulated regional perfusion.

The ILP technique involves a technically complex and invasive operative procedure, requiring open surgical cannulation of the vessels at the root of the extremity. In addition, ILP requires expensive equipment, occupies a surgical operating room for a long period and involves a substantial number of surgical, anesthetic and perfusion staff and nursing personnel. It is only available in specialized centers and is considered less appropriate in elderly patients or those with serious medical co-morbidities. Complications from ILP are not uncommon Significant regional toxicity such as skin necrosis, compartment syndrome and peripheral neuropathy can occur. Vascular catastrophe requiring arterial reconstruction or amputation is uncommon but has been reported.

Isolated limb infusion (LIL) is a low flow, minimally invasive alternative to open complex surgical procedure isolated limb perfusion. Certain differences are evident: ILI is low flow, minimally invasive percuataneous catheters, tourniquet isolation of the extremities and is acidotic and not oxygenated. ILP is high flow, involves an open complex surgical procedure involving open cannulation of the vessels, it is oxygenated, and aerobic. ILI is very repeatable, whereas ILP is difficult to repeat in the same extremity.

SUMMARY

The present application relates to regional treatment of cancer and proliferative disorders and conditions. For example, provided are methods, systems and devices for treating a cancer in a region of a subject. The example systems, methods and devices can be used as alternatives to ILP and low flow rate ILI. For example, provided are high flow rate ILI (HF-ILI) methods and systems.

An example method for treating a cancer in a region of a subject includes percutaneuosly introducing a catheter into the vasculature of the subject, advancing the catheter to, or in proximity to, the region, and infusing fluid through the catheter and into the region, wherein the fluid comprises at least one therapeutic agent effective for treating the cancer. The fluid is infused into the region at a rate of 150 cc/min or higher. Optionally, the therapeutic agent is an anti-cancer agent. Optionally, the catheter is introduced and advanced through an artery of the subject.

Optionally, the method further comprising reducing or eliminating escape of the infused fluid from the region. For example, the escape of infused fluid can be reduced or eliminated by applying a tourniquet proximal to the location where fluid is infused into the region from the catheter. Optionally, the method includes reducing flow of infused fluid through one or more collateral vessels in the region.

Optionally, the catheter is greater than 6 french in size. For example, the catheter is optionally 7, 8, 9, 10, 11 or 12 french in size or is any size in-between 7 and 12 french. The fluid can infused into the region at a rate of between about 150 cc/min and about 600 cc/min. For example, the fluid is optionally infused into the region at 150 cc/min, 160 cc/min, 170 cc/min, 180 cc/min, 190 cc/min, 200 cc/min, 210 cc/min, 220 cc/min, 230 cc/min, 240 cc/min, 250 cc/min, 260 cc/min, 270 cc/min, 280 cc/min, 290 cc/min, 300 cc/min, 310 cc/min, 320 cc/min, 330 cc/min, 340 cc/min, 350 cc/min, 360 cc/min, 370 cc/min, 380 cc/min, 390 cc/min, 400 cc/min, 410 cc/min, 420 cc/min, 430 cc/min, 440 cc/min, 450 cc/min, 460 cc/min, 470, cc/min 480 cc/min, 490 cc/min, 500 cc/min, 510 cc/min, 520 cc/min, 530 cc/min, 540 cc/min, 550 cc/min, 560 cc/min, 570, cc/min 580 cc/min, 590 cc/min, 600 cc/min, or at rates there between.

The fluid is optionally infused, for example, at the rates described herein, for at least 10 minutes. For example, the fluid is optionally infused for 10, 20, 30, 40 minutes or more.

An example method for treating a cancer in a region of a subject includes introducing a catheter into the vasculature of the subject remote from the region, advancing the catheter to or in proximity to the region, and infusing fluid through the catheter and into the region. The fluid comprises at least one therapeutic agent effective for treating the cancer and the catheter is greater than 6 french in size.

Optionally, the catheter is introduced and advanced through an artery of the subject. Optionally, the method further comprising reducing or eliminating escape of the infused fluid from the region. For example, the escape of infused fluid can be reduced or eliminated by applying a tourniquet proximal to the location where fluid is infused into the region from the catheter. Optionally, the method includes reducing flow of infused fluid through one or more collateral vessels in the region.

Optionally, the catheter is greater than 6 french in size. For example, the catheter is optionally 7, 8, 9, 10, 11 or 12 french in size or is any size in-between 7 and 12 french. The fluid can be infused into the region at a rate of between about 150 cc/min and about 600 cc/min. For example, the fluid is optionally infused into the region at 150 cc/min, 160 cc/min, 170 cc/min, 180 cc/min, 190 cc/min, 200 cc/min, 210 cc/min, 220 cc/min, 230 cc/min, 240 cc/min, 250 cc/min, 260 cc/min, 270 cc/min, 280 cc/min, 290 cc/min, 300 cc/min, 310 cc/min, 320 cc/min, 330 cc/min, 340 cc/min, 350 cc/min, 360 cc/min, 370 cc/min, 380 cc/min, 390 cc/min, 400 cc/min, 410 cc/min, 420 cc/min, 430 cc/min, 440 cc/min, 450 cc/min, 460 cc/min, 470, cc/min 480 cc/min, 490 cc/min, 500 cc/min, 510 cc/min, 520 cc/min, 530 cc/min, 540 cc/min, 550 cc/min, 560 cc/min, 570, cc/min 580 cc/min, 590 cc/min, 600 cc/min, or at rates there between.

The fluid is optionally infused, for example, at the rates described herein, for at least 10 minutes. For example, the fluid is optionally infused for 10, 20, 30, 40 minutes or more.

An example system for treating a cancer in a region of a subject includes an intra-vascular catheter and a fluid propulsion apparatus configured to move fluid through the catheter and into the region of the subject. Optionally, the catheter is greater than 6 french in size and the catheter is configured for percutaneous insertion into the vasculature of the subject. The catheter is optionally 7, 8, 9, 10, 11 or 12 french in size or is any size in-between 7 and 12 french.

Optionally, the fluid propulsion apparatus is configured to infuse fluid into the region at a rate of between 150 cc/min and 600 cc/min or at a higher rate. For example, the fluid propulsion apparatus is optionally configured to infuse fluid into the region at 150 cc/min, 160 cc/min, 170 cc/min, 180 cc/min, 190 cc/min, 200 cc/min, 210 cc/min, 220 cc/min, 230 cc/min, 240 cc/min, 250 cc/min, 260 cc/min, 270 cc/min, 280 cc/min, 290 cc/min, 300 cc/min, 310 cc/min, 320 cc/min, 330 cc/min, 340 cc/min, 350 cc/min, 360 cc/min, 370 cc/min, 380 cc/min, 390 cc/min, 400 cc/min, 410 cc/min, 420 cc/min, 430 cc/min, 440 cc/min, 450 cc/min, 460 cc/min, 470, cc/min 480 cc/min, 490 cc/min, 500 cc/min, 510 cc/min, 520 cc/min, 530 cc/min, 540 cc/min, 550 cc/min, 560 cc/min, 570, cc/min 580 cc/min, 590 cc/min, 600 cc/min, or at rates there between.

The catheter is optionally configured for insertion into the vasculature of the subject remote from the region to be treated. Optionally, the fluid propulsion apparatus is a pump or a syringe. For example, the fluid propulsion apparatus is optionally a nonocclusive pump or a pressure differential pump.

A system for treating a cancer in a region of a subject includes an arterial intra-vascular catheter and a fluid propulsion apparatus configured to move fluid comprising a cancer therapeutic agent through the catheter and into the region of the subject. The catheter is greater than 6 french in size and is configured for percutaneous insertion into the vasculature of the subject. Optionally, the arterial catheter is 7, 8, 9, 10, 11 or 12 french in size or is any size in-between 7 and 12 french. The system further comprises a venous catheter. The venous catheter is optionally 7, 8, 9, 10, 11 or 12 french in size or is any size in-between 7 and 12 french.

The fluid propulsion apparatus is configured to infuse fluid into the region at a rate of between 150 cc/min and 600 cc/min or at a higher rate. For example, the fluid propulsion apparatus is configured to infuse fluid into the region at 150 cc/min, 160 cc/min, 170 cc/min, 180 cc/min, 190 cc/min, 200 cc/min, 210 cc/min, 220 cc/min, 230 cc/min, 240 cc/min, 250 cc/min, 260 cc/min, 270 cc/min, 280 cc/min, 290 cc/min, 300 cc/min, 310 cc/min, 320 cc/min, 330 cc/min, 340 cc/min, 350 cc/min, 360 cc/min, 370 cc/min, 380 cc/min, 390 cc/min, 400 cc/min, 410 cc/min, 420 cc/min, 430 cc/min, 440 cc/min, 450 cc/min, 460 cc/min, 470, cc/min 480 cc/min, 490 cc/min, 500 cc/min, 510 cc/min, 520 cc/min, 530 cc/min, 540 cc/min, 550 cc/min, 560 cc/min, 570, cc/min 580 cc/min, 590 cc/min, 600 cc/min, or at rates there between.

Optionally, the catheter is configured for insertion into the vasculature of the subject remote from the region to be treated. Optionally, the fluid propulsion apparatus is a pump or a syringe. For example, the fluid propulsion apparatus is optionally a nonocclusive pump. The fluid propulsion apparatus is optionally a pressure differential pump.

Also provided is a fluid circuit for delivering a cancer therapeutic to a region of a subject. An example circuit includes a venous catheter positionable within a vein in the region of the subject and an arterial catheter positionable within an artery in the region of the subject. The circuit further includes a pump in communication with the venous catheter and arterial catheter, wherein activation of the pump causes fluid comprising the cancer therapeutic to circulate through the venous catheter, arterial catheter and region of the subject at rate of 150 cc/minutes or greater.

The venous catheter is optionally 7, 8, 9, 10, 11 or 12 french in size or is any size in-between 7 and 12 french. The arterial catheter is optionally 7, 8, 9, 10, 11 or 12 french in size or is any size in-between 7 and 12 french.

The pump is optionally configured to infuse fluid into the region at a rate of between 150 cc/min and 600 cc/min or at a higher rate. For example, the pump is optionally configured to infuse fluid into the region at 160 cc/min, 170 cc/min, 180 cc/min, 190 cc/min, 200 cc/min, 210 cc/min, 220 cc/min, 230 cc/min, 240 cc/min, 250 cc/min, 260 cc/min, 270 cc/min, 280 cc/min, 290 cc/min, 300 cc/min, 310 cc/min, 320 cc/min, 330 cc/min, 340 cc/min, 350 cc/min, 360 cc/min, 370 cc/min, 380 cc/min, 390 cc/min, 400 cc/min, 410 cc/min, 420 cc/min, 430 cc/min, 440 cc/min, 450 cc/min, 460 cc/min, 470, cc/min 480 cc/min, 490 cc/min, 500 cc/min, 510 cc/min, 520 cc/min, 530 cc/min, 540 cc/min, 550 cc/min, 560 cc/min, 570, cc/min 580 cc/min, 590 cc/min, 600 cc/min, or at rates there between. The pump is optionally a nonocclusive pump. The pump is optionally a pressure differential pump.

These and other features and advantages of the present invention will become more readily apparent to those skilled in the art upon consideration of the following detailed description and accompanying drawings, which describe both the preferred and alternative embodiments of the present invention.

DETAILED DESCRIPTION

The present invention now will be described more fully hereinafter with reference to specific embodiments of the invention. Indeed, the invention can be embodied in many different forms and should not be construed as limited to the embodiments set forth herein; rather, these embodiments are provided so that this disclosure will satisfy applicable legal requirements.

As used in the specification, and in the appended claims, the singular forms "a," "an," "the," include plural referents unless the context clearly dictates otherwise.

The term "comprising" and variations thereof as used herein are used synonymously with the term "including" and variations thereof and are open, non-limiting terms.

Provided are methods for treating a cancer in a region of a subject. Although ILP is effective in this regard, it is an invasive, complex, and costly procedure. In response to the difficulties associated with ILP, a simplified and minimally invasive procedure called isolated limb infusion (ILI) was developed with the objective of obtaining the benefits of ILP without incurring its major disadvantages.

ILI is a non-oxygenated, low-flow, anoxic procedure performed via percutaneously inserted catheters. Despite the brief exposure time of the tissues to melphalan during ILI (20-30 minutes), theory and practice have shown that there is adequate cellular drug uptake for effective tumor cell killing to be achieved in most patients.

This disclosure is related to high flow rate ILI (HF-ILI), which uses infusion flow rates greater than conventional ILI procedures. An example HF-ILI method comprises percutaneuosly introducing a catheter into the vasculature of a subject and advancing the catheter to, or in proximity to, the region. As used throughout, by a subject is meant an individual. A patient refers to a subject afflicted with a disease or disorder. The term patient includes human and veterinary subjects.

Figure 1A:
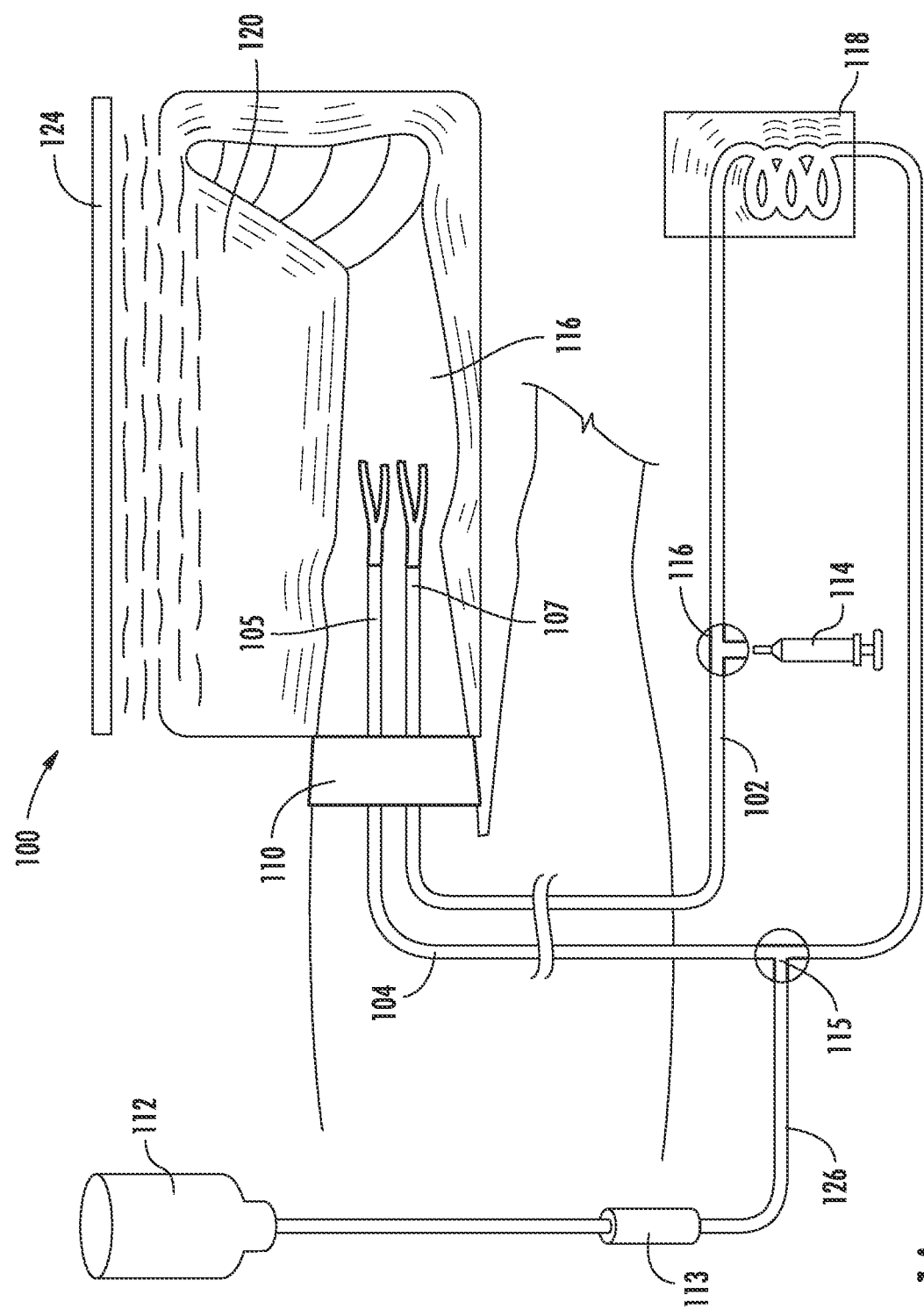
FIG. 1A is a schematic illustration of an example high flow rate isolated limb infusion (HF-ILI) circuit.
Figure 1B:
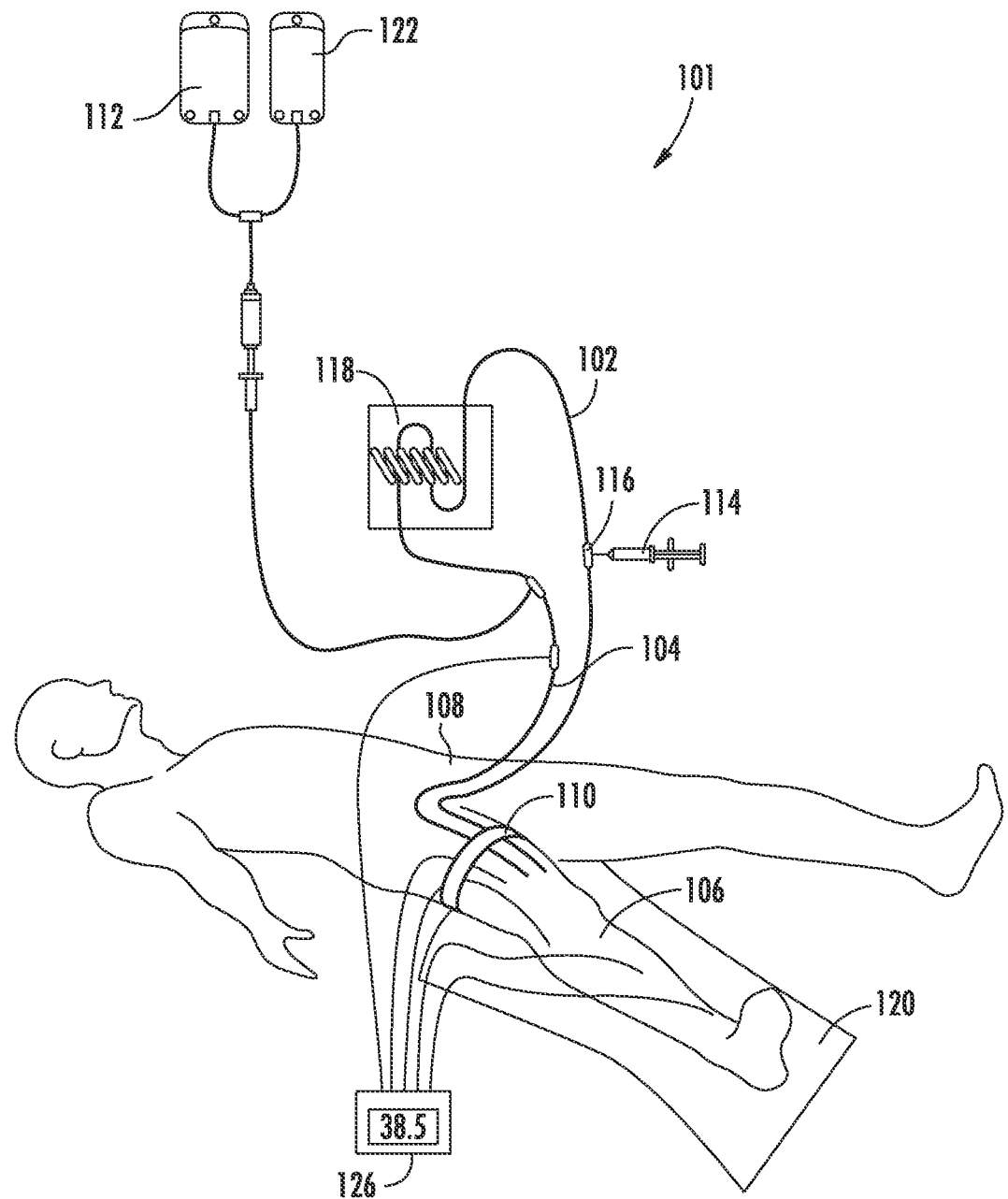
FIG. 1B is a schematic illustration of an example HF-ILI circuit.

Referring to FIGS. 1A and 1B, the systems 100 and 101 comprise an arterial catheter 104 and a venous catheter 102 that can be advanced into a limb 116 of the subject. The limb can be an arm or a leg. The limb can be afflicted with cancer or another proliferative disease or disorder. The region to be treated can also be an organ such as a liver or portion thereof that can be vascularly isolated from the subject's systemic circulation.

Once advanced into the region, a fluid 112 comprising at least one therapeutic agent is infused through the arterial catheter 104 and into the region. The therapeutic agent is optionally effective for treating the cancer. A variety of therapeutic agents can be used. For example agents used in ILP or conventional ILI can be used with the disclosed HF-ILI methods, systems and devices.

The specific therapeutically effective dose level for any particular patient may depend upon a variety of factors including the disorder being treated and the severity of the disorder; activity of the specific compound employed; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. The dosage can be adjusted by the individual physician. Dosage can vary, and can be administered in one or more dose administrations daily, for one or several days. Guidance can be found in the literature for appropriate dosages for given classes of pharmaceutical products. The dosage can also be determined for new therapeutic agents using, for example, the above considerations.

Optionally, the fluid is infused into the region at a rate of 150 cc/min or higher. In this regard, the methods described herein are optionally referred to as High Flow Rate Isolated Limb Infusion (HF-ILI), which means that flow rates of at least 150 cc/min can be used to treat a regional lesion in a subject. Optionally, the flow rates are constant, for example, during the duration of one or more treatment protocols.

The arterial and/or venous catheter used for HF-ILI are optionally greater than 6 french in size. For example, the either or both the arterial and venous catheters are optionally 7, 8, 9, 10, 11 or 12 french in size or is any size in-between 7 and 12 french. Optionally, the arterial and venous catheters are matched in size such that the same size french catheter is used on the arterial and venous sides of the circuit. Optionally, the arterial and venous catheters differ in french size.

As noted above, the fluid can be infused at a predetermined rate. For example, the fluid is optionally infused into the region at a rate of between 150 cc/min and 600 cc/min. Therefore, optionally, the fluid is infused into the region at 150 cc/min, 160 cc/min, 170 cc/min, 180 cc/min, 190 cc/min, 200 cc/min, 210 cc/min, 220 cc/min, 230 cc/min, 240 cc/min, 250 cc/min, 260 cc/min, 270 cc/min, 280 cc/min, 290 cc/min, 300 cc/min, 310 cc/min, 320 cc/min, 330 cc/min, 340 cc/min, 350 cc/min, 360 cc/min, 370 cc/min, 380 cc/min, 390 cc/min, 400 cc/min, 410 cc/min, 420 cc/min, 430 cc/min, 440 cc/min, 450 cc/min, 460 cc/min, 470 cc/min, 480 cc/min, 490 cc/min, 500 cc/min, 510 cc/min, 520 cc/min, 530 cc/min, 540 cc/min, 550 cc/min, 560 cc/min, 570, cc/min 580 cc/min, 590 cc/min, 600 cc/min, or at rates there between.

The catheter 104 used to deliver the fluid is introduced and advanced through an artery of the subject. A venous catheter 102 is also percutaneously introduced and advanced through the veins of the subject to the region. The arterial 104 and venous 102 catheters can be placed in fluid communication within a HF-ILI circuit.

Still referring to FIGS. 1A and 1B, example circuits comprise an extra-corporal portion. The extra-corporal portion optionally comprises tubing, valves, stop cocks and a syringe 114. The HF-ILI circuits also comprise a corporal portion which includes the terminal portions of the arterial and venous catheters and the vasculature of the limb.

A full HF-ILI circuit allows for fluid comprising a therapeutic agent 112 to enter the subject through the arterial catheter 104 and to be removed from the subject through the venous catheter 102. The fluid (also referred to as an infusate) containing the therapeutic agent, such as a chemotherapeutic agent, and the patient's blood can be circulated into and out of the subject, e.g. circulated through the circuit, using a fluid forcing device such as the syringe 114.

The fluid circulated through the circuit can be heated using a warming device such as a warming coil 118. The limb can also be heated, for example, by using an external heater 124 and/or a heating blanket 120. A variety of valves or three-way stop cocks can be used to coordinate movement of fluid through the circuit. These valves and/or stop cocks can be located at positions of the circuit such as the junction 115 of a line 126 from the fluid source and the extra-corporal circuit tubes or at the junction 116 of the syringe or pumping apparatus and the extra-corporal circuit. For example, valves and/or stop cocks can be used to direct fluid movement in a desired direction upon actuation of the syringe 114 or another pumping apparatus. The methods, systems and devices described herein are not limited to circuits containing specific features and one skilled in the art will appreciate that a variety of circuit architectures can be used while providing HF-ILI flow rates described herein.

To reduce or prevent systemic exposure to the therapeutic agent, escape of the fluid from the region can be reduced or eliminated. For example, a tourniquet 110 may be applied proximal to the location where fluid is infused into the region from the arterial catheter 104. The catheters each have a portion (105 and 107) distal to the tourniquet.

Systemic exposure can be further reduced or eliminated by reducing flow of infused fluid through one or more of the subject's collateral vessels in the region. For example, selective embolization can be used to eliminate or reduce flow through one or more of the subject's collateral vessels in the region.

Figure 2:
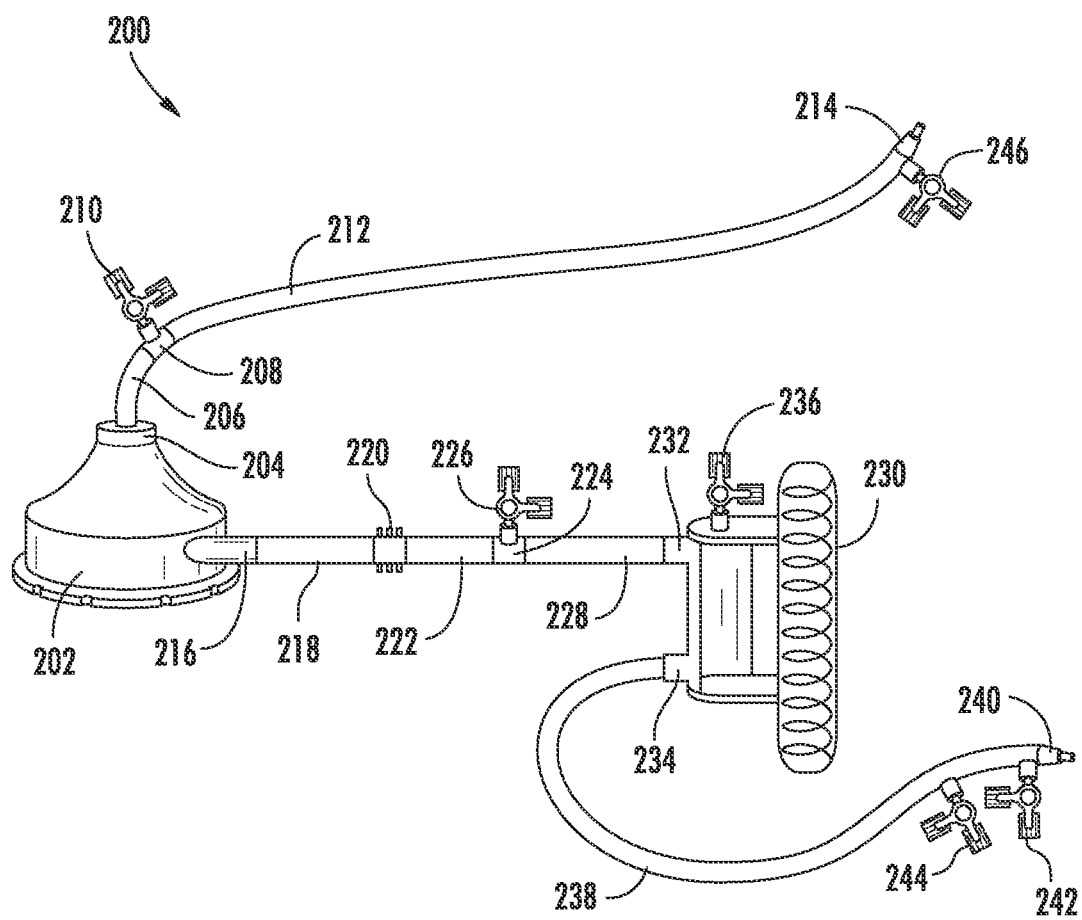
FIG. 2 is a schematic illustration of an example pump-assisted HF-ILI circuit.

FIG. 2 is a schematic illustration of an example pump-assisted HF-ILI circuit 200. Similar to the circuits described above, the pump-assisted HF-ILI circuit shown in FIG. 2 is optionally used to perform isolated limb infusion with a fluid comprising one or more chemotherapeutic agents with infusion rates at or above 150 cc/min.

For example, using the system of FIG. 2 fluid, comprising a chemotherapeutic agent, can be infused through a region of a subject at a predetermined rate. The fluid is optionally infused into the region at a rate of between 150 cc/min and 600 cc/min. Therefore, optionally, the fluid is infused into the region at 150 cc/min, 160 cc/min, 170 cc/min, 180 cc/min, 190 cc/min, 200 cc/min, 210 cc/min, 220 cc/min, 230 cc/min, 240 cc/min, 250 cc/min, 260 cc/min, 270 cc/min, 280 cc/min, 290 cc/min, 300 cc/min, 310 cc/min, 320 cc/min, 330 cc/min, 340 cc/min, 350 cc/min, 360 cc/min, 370 cc/min, 380 cc/min, 390 cc/min, 400 cc/min, 410 cc/min, 420 cc/min, 430 cc/min, 440 cc/min, 450 cc/min, 460 cc/min, 470, cc/min 480 cc/min, 490 cc/min, 500 cc/min, 510 cc/min, 520 cc/min, 530 cc/min, 540 cc/min, 550 cc/min, 560 cc/min, 570, cc/min 580 cc/min, 590 cc/min, 600 cc/min, or at rates there between.

The circuit 200 includes a pump 202. The pump 202 includes and inlet portion 204 and an outlet portion 216. The pump is used to drive fluid through the circuit and through the region of the subject that is to be treated by HF-ILI. For example, the pump is optionally adjustable such that the rate of fluid flow through the circuit is at least 150 cc/min and up to and including 600 cc/min, for example.

As described herein, the term circuit can include portions of the described devices positioned external to the subject being treated, portions of the described devices positioned inside the subject, and portions of the subject's vasculature. In use, all of these portions allow for fluid to be circulated through the region of the subject that is targeted for treatment, such as regions of the subject afflicted with cancerous cells.

Optionally, the pump is a nonocclusive pump. Optionally, the pump is a pressure differential pump. For example, a nonocclusive centrifugal blood pump is optionally used. Such a pump promotes laminar flow. The pump is optionally a Bio-Pump® (Medtronic, Minneapolis, Minn.). For example, the pump is optionally a Bio-Pump® Plus BPX80 or BPX50 nonocclusive pump. Optionally, the pump is used with one or more of a Bio-Console® (Medtronic, Minneapolis, Minn.) speed controller, a bubble detector cable, a level sensor, a flow transducer, a dual channel pressure monitor, an external drive motor, and a hand crank.

The pump optionally uses an AC power source and includes a brushless DC pump drive motor. The pump can provide the desired flow rates without causing collapse of the veins in which the large bore venous catheters are located. For example, the pump can be used to circulate fluid comprising a chemotherapeutic agent through the vasculature of a subject at a rate of at least 150 cc/minute using a venous catheter of 6 french or larger without causing collapse of the vein that the catheter is inserted into. The pump can be integrated with a console such as the Bio-Console®, which can receive user input causing adjustment of operating parameters of the pump. For example, the revolutions per minute of the pump can be adjusted up or down to achieve a desired flow rate between 150 cc/min and 600 cc/min. The fluid optionally comprises blood, chemotherapy, and one or more carrier or diluents.

The catheters used are such as those described throughout. The catheters can vary in length. For example, the catheters can be up to sixty centimeters in length or longer. The length of the catheters can be determined for example depending on factors such as the region of the subject being treated and the size of the subject. Such catheters are known in the art and, for example, are used in interventional radiology procedures.

The portion of the circuit external to the subject includes a venous segment (206, 208, 210, 212, and 214). Although not shown in FIG. 2, the venous circuit can further include a catheter placed in the subject and attached at 214. The venous catheter (not shown) is attachable at the male luer 214, which itself is attached to the medical grade fluid conduit segment 212. Optionally, the conduit 212 is medial grade tubing having predetermined dimensions of 3/16 inch internal diameter, by 1/16 inch wall thickness, by four or more feet long. Other dimensions can also be used while still allowing the desired flow rates.

The conduit segment 212 is attached to a linker segment 208 such as a luer linker, which, in addition to the conduit segment 212, allows passage of fluid there through. The linker segment 208 is in fluid communication with a 3-way stop cock 210 that can be adjusted to control fluid flow through the circuit and can also be used to direct fluid flow out of the circuit, for example, to a pressure detection device that can be used to detect and monitor pressure within the circuit. For example, a Medtronic (Minneapolis, Minn.) DLP or dual channel pressure monitor can be used. Pressure monitors are optionally configured for use with the particular pump used in the circuit. The venous segment further includes a conduit segment 206 that fluidly connects the linker segment to the inlet of the pump 202.

The portion of the circuit external to the subject also includes an arterial segment (218, 220, 222, 224, 226, 228, 232, 236, 230, 234, 238 and 240. The arterial segment is used to deliver fluid from the pump into the arterial system of a subject. A conduit 218 is attached to the outlet 216 to receive fluid delivered from the pump 202. The fluid moves through the conduit 218 and through a flow probe 220. The flow probe 220 can be used to detect and/or monitor fluid flow rate through the circuit. For example, the flow probe can be used to indicate a flow rate of about 150 cc/min or higher. The flow probe can be configured for use with the particular pump used and thus be calibrated to provide accurate flow readings for flow through the circuit.

A conduit 222 can be used to connect the flow probe to a linker conduit segment 224 or linker luer, which is in fluid communication with a 3-way stop cock 226. As described with respect to the venous branch of the circuit, the 3-way stop cock 226 can be adjusted to control fluid flow through the circuit and can also be used to direct fluid flow out of the circuit, for example, to a pressure detection device that can be used to detect and monitor pressure within the circuit.

The arterial segment further includes a conduit segment 228 that fluidly connects the linker segment to the inlet 232 of a heat exchange unit 230. Fluid flows through the heat exchange unit 230 and exits at the outlet 234. As fluid flows through the heat exchange unit, it can be warmed or cooled to a desired temperature. For example, the fluid can be warmed to a desired temperature to help maintain the limb at a desired treatment temperature. A desired limb treatment temperature may, for example, be about 37 C. In this regard, the fluid passing through the circuit can be warmed above normothermic. For example, the fluid in the circuit is optionally warmed at the heat exchange unit to temperatures above 37 C. For example, the heat exchange unit can be warmed to about 42 C causing warming of the fluid flowing there through to near 42 C. The fluid flowing through the circuit optionally is warmed to between 40 and 42 C.

Example heat exchangers include those for warming blood. For example, optional heat exchangers include ECMO® (Medtronic, Minneapolis, Minn.). The outlet 234 of the heat exchange unit is attached to a conduit segment 238, which terminates in a male luer 240. The male luer can be attached to an arterial catheter as described herein for delivering fluid into the arterial system of the subject. A 3-way stop cock 236 may also be located at the heat exchanger where it is optionally used to eliminate air from the circuit.

The arterial catheter can further comprise one or more 3-way stop cocks (244 and 242) integral with the male luer 240 or positioned between the heat exchange unit and the male luer. The 3-way stop cocks can be used to stop fluid flow through the circuit and to push chemotherapeutic agent and flush agents into the circuit. For example, the chemotherapeutic agent can be added to the system by attaching the chemotherapeutic agent or source thereof to a stop cock on the arterial side distal to the heat exchanger. The stop cock is opened and the agent is pushed into the circuit. The stop cock can be closed and another stop cock opened to push flush into the circuit. The circuit can then be allowed to run for a given duration and additional chemotherapeutic agent and flush can be introduced into the circuit until the desired dosage has been introduced into the circuit.

The circuit can be primed using gravity. For example, the stop cocks at the male luers can be used to shut off circulation through the circuit. An IV administration set with fluid can be attached to the venous side of the circuit and the IV bag of the set can be raised above the circuit. Then the stop cock at the arterial end can be opened allowing the circuit to fill with fluid, such as saline, before being attached to the venous and arterial catheters which are previously positioned in the desired region of the subject. Optionally, the venous and arterial catheters are placed within the subject prior to connection to the external portions of the circuit shown in FIG. 2. The full volume of the circuit is optionally about 300 to 400 milliliters.

EXAMPLES

Example 1

High flow rate ILI is performed to regionally treat cancer in a subject. A schematic overview of systems 100 and 101 for performing the procedure are show in FIGS. 1A and 1B. Briefly, the technical details are as follows: catheters 102 and 104 with additional side-holes near their tips are inserted percutaneously into the axial artery 104 and vein 102 of the disease-bearing limb 106 via the contralateral groin 108, and their tips are positioned in such a way that they are at the level of the knee or elbow joint. The catheters are optionally greater than 6 french in size and the flow rates are 150 cc/min or higher. Tissues more proximally located in the limb but distal to the level of the tourniquet 110 are perfused in a retrograde fashion via collateral vascular channel.

Prior to infusion and completing the closed circuit with the catheters, the patient is given a general anesthetic, and heparin (3 mg/kg) is infused to achieve full systemic heparinization. Optionally, a single 5 mg IV dose of tropisetron, a 5HT3 antagonist, is administered as prophylaxis against postoperative nausea and vomiting.

A pneumatic tourniquet 110 is inflated around the root of the limb to be treated and the fluid 112 comprising a therapeutic agent, such as a cytotoxic agent is infused into the isolated circuit via the arterial catheter 104. Example cytotoxic drugs are melphalan 5-10 mg/l of tissue (e.g., 7.5 mg/l) and actinomycin-D 50-100 µg/l of tissue (e.g., 75 µg/l) in 400 mL warmed, heparinized normal saline.

A dose of melphalan of about 7.5 mg/l volume lower extremity and 10 mg/l upper extremity can be used. The dosage can be adjusted based on patient characteristics, such as those described above, one example being ideal body weight. These principles are applied in determining melphalan dosages for high flow rate ILI. Actinomycin-D can be used as well because of the good response rates (CR 73%) of the melphalan/actinomycin-D combination when administered by conventional ILP.

For the duration of the high flow rate ILI procedure (20-30 minutes), the infusate is continually circulated by repeated aspiration from the venous catheter 102 and reinjection into the arterial catheter 104 using a syringe 114 attached to a three-way tap 116 in the external circuit. During the procedure, fluid can be infused at a predetermined rate. For example, the fluid is optionally infused into the region at a rate of between 150 cc/min and 600 cc/min. Therefore, optionally, the fluid is infused into the region at 150 cc/min, 160 cc/min, 170 cc/min, 180 cc/min, 190 cc/min, 200 cc/min, 210 cc/min, 220 cc/min, 230 cc/min, 240 cc/min, 250 cc/min, 260 cc/min, 270 cc/min, 280 cc/min, 290 cc/min, 300 cc/min, 310 cc/min, 320 cc/min, 330 cc/min, 340 cc/min, 350 cc/min, 360 cc/min, 370 cc/min, 380 cc/min, 390 cc/min, 400 cc/min, 410 cc/min, 420 cc/min, 430 cc/min, 440 cc/min, 450 cc/min, 460 cc/min, 470, cc/min 480 cc/min, 490 cc/min, 500 cc/min, 510 cc/min, 520 cc/min, 530 cc/min, 540 cc/min, 550 cc/min, 560 cc/min, 570, cc/min 580 cc/min, 590 cc/min, 600 cc/min, or at rates there between.

Limb temperature is increased by incorporating a blood-warming coil 118 in the extracorporeal circuit and by encasing the limb in a hot-air blanket 120, with a radiant heater placed over it.

After 20-30 minutes, the limb is flushed with one liter of Hartmann's solution 122 via the arterial catheter 104, and the venous effluent is discarded. For example, the limb can be infused for 30 minutes prior to flushing. The limb tourniquet 110 is then deflated to restore normal limb circulation, the heparin is reversed with protamine, and the catheters are removed. For patients with metastatic disease in the groin or axilla requiring a regional lymph node dissection as well as a high flow rate ILI, this can be undertaken under the same anesthetic after completion of the high flow rate ILI procedure, removal of the catheters (102 and 104), and reversal of heparin.

Subcutaneous and intramuscular limb temperatures are monitored continuously during the high flow rate ILI procedure, and blood samples are optionally taken at regular intervals to measure the melphalan concentrations and blood gases. The drug leakage rate from the isolated limb into the systemic circulation is optionally assessed retrospectively in all patients, on the basis of systemic melphalan concentrations that can be measured routinely during each procedure.

Example 2

Venous 102 and arterial 104 catheters are placed percutaneously in a subject for regional treatment of cancer in a subject by high flow rate isolated limb infusion (HF-ILI). The arterial catheter 104 can be greater than 6 french in size. For example, a 7 french arterial catheter can be used. The venous catheter 102 can also be 6 french in size or greater. For example, a 7 french venous catheter can be used.

The catheters (102 and 104) can be inserted percutaneously at a site remote from the region to be treated. For example, an ipsilateral popliteal or a contralateral femoral approach can be used for treating an arm or a leg.

Flouroscopy can be used to navigate the catheters (102 and 104) from the insertion site to the region to be treated. Optionally, fluoroscopy times can be reduced using a popliteal approach. For example, the time can be reduced from a median of 17.9 to 8.3 minutes; range (P=0.0019) resulting in significantly less exposure to the radiologist and patient.

The HF-ILI circuit can further comprise one way valves and three way stop cocks to control flow of fluid through the circuit. A heating source 118 can be used to warm fluid in the circuit and a heater 124 and a heating blanket 120 can be used to warm the limb that is being treated. For example, a heating bath with an in-line cardiac heat exchanger can be used to warm the fluid. The temperature of the fluid can be monitored using a thermometer 126 that is within the circuit.

Optionally, the circuit comprises a perfusion machine to force fluid through the circuit. A syringe or a pump can also be used to force fluid through the circuit.

A tourniquet 110 can be applied to an extremity proximal to the opening of the catheters in the region to be treated. The tourniquet can be used to reduce systemic exposure of a therapeutic agent, such as an anti-cancer drug. The tourniquet can be optionally applied at 300 mmHg to a lower extremity and 250 mmHg to an upper extremity. The patient can also be heparinized and the patients ACT can be optionally calculated. For example, the patient can be anti-coagulated to an ACT over 400 seconds. The heparin can be later reversed by protamine use.

The completed circuit is used to perform HF-ILI. For example, after fully heparinizing the patient and then completing the circuit, the circuit can be primed with blood. Once the tourniquet is applied the subject's pedal pulse can be monitored to see that it disappears. For example, Doppler can be used to determine if the tourniquet has closed the artery supplying the limb. One skilled in the art will appreciate that the pulse can be monitored in other arteries supplying the limb to be treated. Next, 60 mg papaverine can be infused through the arterial side, followed by an infusion of chemotherapy. The fluid including chemotherapy can be circulated through corporal and extra-corporal portions of the circuit for about 30 minutes. The fluid can be infused at a predetermined rate. For example, the fluid is optionally infused into the region at a rate of between 150 cc/min and 600 cc/min. Therefore, optionally, the fluid is infused into the region at 150 cc/min, 160 cc/min, 170 cc/min, 180 cc/min, 190 cc/min, 200 cc/min, 210 cc/min, 220 cc/min, 230 cc/min, 240 cc/min, 250 cc/min, 260 cc/min, 270 cc/min, 280 cc/min, 290 cc/min, 300 cc/min, 310 cc/min, 320 cc/min, 330 cc/min, 340 cc/min, 350 cc/min, 360 cc/min, 370 cc/min, 380 cc/min, 390 cc/min, 400 cc/min, 410 cc/min, 420 cc/min, 430 cc/min, 440 cc/min, 450 cc/min, 460 cc/min, 470, cc/min 480 cc/min, 490 cc/min, 500 cc/min, 510 cc/min, 520 cc/min, 530 cc/min, 540 cc/min, 550 cc/min, 560 cc/min, 570, cc/min 580 cc/min, 590 cc/min, 600 cc/min, or at rates there between. The circuit can then be flushed and the tourniquet can be released.

The described circuits in this example and through the specification can be used to perform HF-ILI using minimally invasive techniques. For example, the circuits can be used to treat locally recurrent and metastatic melanoma isolated to one limb. The catheters (102 and 104) are percutaneously introduced and chemotherapy can be infused for about 30 minutes. Table 1 shows some aspects of HF-ILI (left column) versus the more complicated and expensive and medically risky procedure of isolated limb perfusion (right column)

TABLE 1

| Minimally invasive small caliber percutaneously placed catheters | Open surgical procedure with large bore catheters, more complex |
|---|---|
| Shorter operative and perfusion times<br>Hypoxic, acidotic conditions<br>High flow<br>Mild hyperthermia<br>Easy to repeat procedure | Longer operative and perfusion times<br>Aerobic, oxygenated<br>High flow<br>Hyperthermia<br>Difficult to repeat |

Dosing for HF-ILI can be determined using factors such as water displacement and serial circumferential measurements. Dosing is optionally corrected for ideal body weight (cIBW). Example dosing of Melphalan is 7.5 mg/l for a lower extremity and 10 mg/l for an upper extremity. An example dose of Actinomycin D is 100 ug/l for both a lower and upper extremity.

As described, the systems, methods and devices described herein can be used to treat regional cancer. An example cancer that can be treated is melanoma. Other example cancers that can be treated are an unresectable sarcoma, a Merkel cell carcinoma, advanced SCCA, and adnexal skin cancers.

Many modifications and other embodiments of the invention set forth herein will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for treating a cancer in a vascularly isolated region of a subject, the vascularly isolated region being isolated by at least one tourniquet, the method comprising:
   a. percutaneously introducing a catheter into a vasculature of the subject;
   b. advancing the catheter to or in proximity to the vascularly isolated region, wherein the catheter is introduced and advanced through an artery of the subject; and
   c. infusing and continuously recirculating fluid through the catheter and into the vascularly isolated region, wherein the fluid comprises at least one therapeutic agent effective for treating the cancer, and wherein the fluid is infused into the vascularly isolated region at a rate of 160 cc/min or higher.

2. The method of claim 1 further comprising reducing or eliminating escape of the infused fluid from the vascularly isolated region.

3. The method of claim 2, wherein the tourniquet is applied proximal to a location where the fluid is infused into the vascularly isolated region from the catheter.

4. The method of claim 3, further comprising reducing flow of the infused fluid through one or more collateral vessels in the vascularly isolated region.

5. The method of claim 1, wherein the therapeutic agent is an anti-cancer agent.

6. The method of claim 1, wherein the catheter is greater than 6 french in size.

7. The method of claim 6, wherein the catheter is 7, 8, 9, 10, 11 or 12 french in size or is any size in-between 7 and 12 french.

8. The method of claim 1, wherein the fluid is infused into the vascularly isolated region at a rate of between 160 cc/min and 600 cc/min.

9. The method of claim 1, wherein the fluid is infused for at least 10 minutes.

10. The method of claim 9, wherein the fluid is infused for 10, 20, 30, 40 minutes or more.

11. A method for treating a cancer in a vascularly isolated region of a subject, the vascularly isolated region being isolated by at least one tourniquet, the method comprising:
   a. percutaneously introducing a catheter into a vasculature of the subject remote from the vascularly isolated region;
   b. advancing the catheter to or in proximity to the vascularly isolated region; and
   c. infusing and continuously recirculating fluid through the catheter and into the vascularly isolated region, wherein the fluid comprises at least one therapeutic agent effective for treating the cancer, and wherein the fluid is infused into the vascularly isolated region at a rate of 160 cc/min or higher.

12. A system for treating a cancer in a vascularly isolated region of a subject, the vascularly isolated region being isolated by at least one tourniquet, the system comprising:
   a. an intra-vascular catheter; and
   b. a fluid propulsion apparatus configured to infuse and continuously recirculate fluid through the intra-vascular catheter and into the vascularly isolated region of the subject, wherein the catheter is configured for percutaneous insertion into a vasculature of the subject and wherein the fluid is infused into the vascularly isolated region at a rate of 160 cc/min or higher.

13. The system of claim 12, wherein the intra-vascular catheter is further configured for insertion into the vasculature of the subject remote from the vascularly isolated region to be treated.

14. The system of claim 12, wherein the fluid propulsion apparatus is a pump or a syringe.

15. The system of claim 12, wherein the fluid propulsion apparatus is a nonocclusive pump.

16. The system of claim 12, wherein the fluid propulsion apparatus is a pressure differential pump.

* * * * *